US 7,519,435 B2

(12) United States Patent
Parker et al.

(10) Patent No.: US 7,519,435 B2
(45) Date of Patent: Apr. 14, 2009

(54) METHODS FOR MAINTAINING LOW IMPEDANCE OF ELECTRODES

(75) Inventors: John L. Parker, Roseville (AU); Dusan Milojevic, Westleigh (AU)

(73) Assignee: Cochlear Limited, Lane Cove, NSW (AU)

( * ) Notice: Subject to any disclaimer, the term of this patent is extended or adjusted under 35 U.S.C. 154(b) by 209 days.

(21) Appl. No.: 11/159,256

(22) Filed: Jun. 23, 2005

(65) Prior Publication Data
US 2006/0004432 A1    Jan. 5, 2006

(30) Foreign Application Priority Data
Jun. 23, 2004    (AU) .............................. 2004903437

(51) Int. Cl.
*A61N 1/05* (2006.01)
(52) U.S. Cl. ........................ 607/137; 607/115; 607/121
(58) Field of Classification Search ................. 607/121, 607/137, 2, 115, 116
See application file for complete search history.

(56) References Cited

U.S. PATENT DOCUMENTS

| 5,653,742 | A | * | 8/1997 | Parker et al. ................. 607/137 |
| 5,786,439 | A | * | 7/1998 | Van Antwerp et al. ........ 528/77 |
| 5,833,714 | A | * | 11/1998 | Loeb ........................... 607/56 |
| 5,853,424 | A | * | 12/1998 | Rise ........................... 607/117 |
| 6,116,413 | A | * | 9/2000 | Tabor et al. ................. 206/205 |
| 6,304,786 | B1 | * | 10/2001 | Heil et al. .................... 607/126 |
| 6,304,787 | B1 | * | 10/2001 | Kuzma et al. ............... 607/137 |
| 6,354,299 | B1 | * | 3/2002 | Fischell et al. .............. 128/899 |
| 6,497,729 | B1 | * | 12/2002 | Moussy et al. ........... 623/23.57 |
| 7,218,971 | B2 | * | 5/2007 | Heil et al. .................... 607/121 |

* cited by examiner

*Primary Examiner*—Carl H Layno
*Assistant Examiner*—Brian T Gedeon
(74) *Attorney, Agent, or Firm*—Connolly Bove Lodge & Hutz LLP

(57) ABSTRACT

An implantable tissue-stimulating device for an implantee. The device comprising an elongate member having at least one electrode. At least a portion of the device is coated with a coating that at least partially inhibits adhesion of organic molecules to the device following implantation.

32 Claims, 5 Drawing Sheets

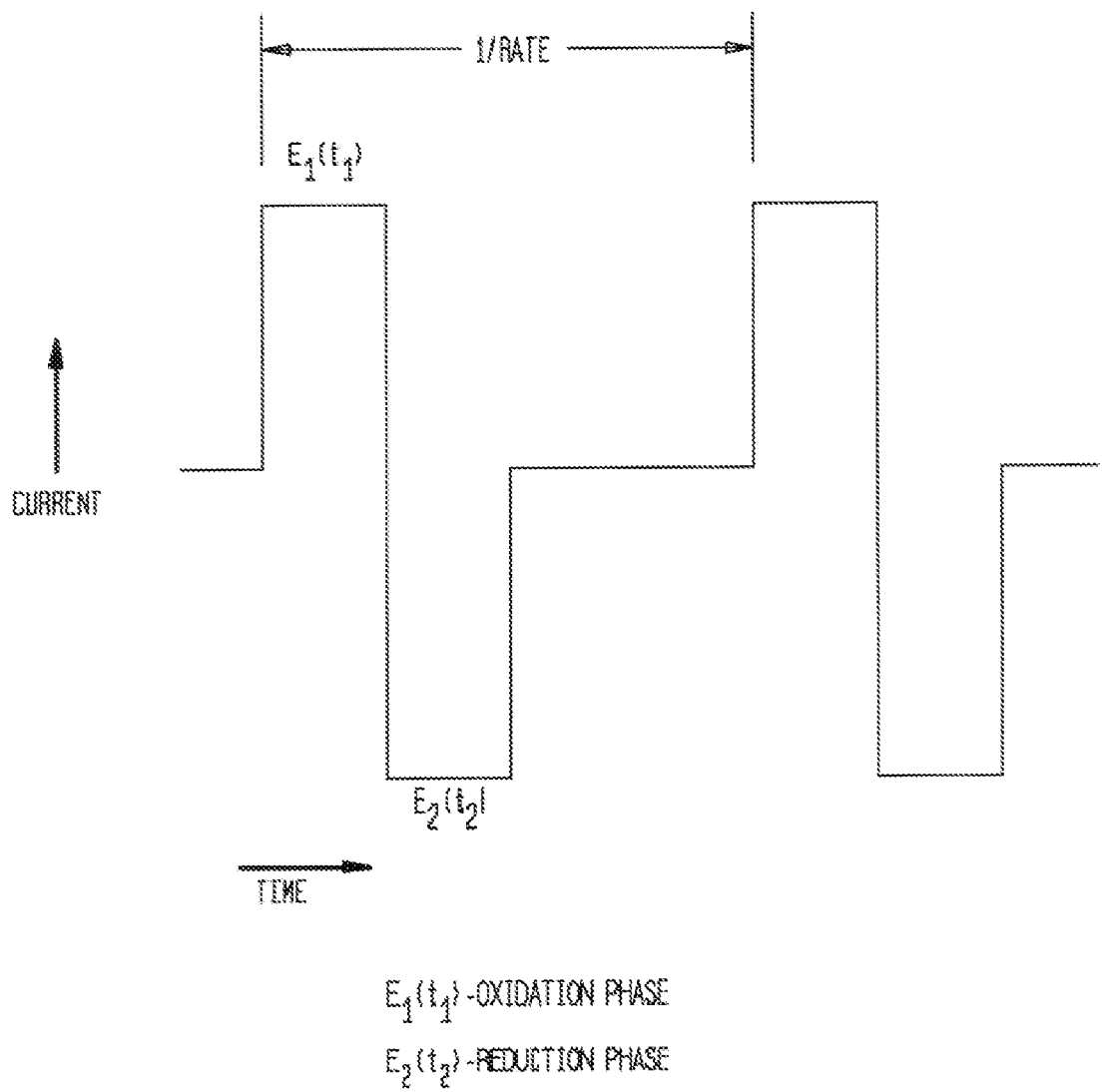

METHODS FOR MAINTAINING LOW IMPEDANCE OF ELECTRODES

CROSS-REFERENCE TO RELATED APPLICATIONS

This application makes reference to and claims the priority of Australian Provisional Application No. 2004903437, entitled, "Methods for Maintaining Low Impedance of Electrodes," filed Jun. 23, 2004. The entire disclosure and contents of the above applications are hereby incorporated by reference.

BACKGROUND

1. Field of Invention

The present application relates to an implantable apparatus, such as a hearing implant, that delivers electrical stimulation to an implantee.

2. Related Art

Studies have demonstrated that a build up of tissue growth does occur on and/or around the electrodes of a hearing implant electrode array following implantation. This can occur as a consequence of some interaction between the body and the implant, perhaps as a result of an injury to the body caused by the implantation or simply due to deposition of organic molecules from the perilymph within the cochlea. Whatever the reason, the deposition of material on the electrodes following implantation will in most instances increase the impedance of the electrodes and so influence the power consumption and efficiency of the hearing implant.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

SUMMARY

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

In a first aspect, the present invention is an implantable tissue-stimulating device for an implantee comprising an elongate member having at least one electrode, wherein at least a portion of the device is coated with a coating that at least partially inhibits adhesion of organic molecules to said device following implantation.

In a second aspect, the invention is a method of modifying the Surface of at least a portion of a tissue stimulating device, the method comprising coating said portion with a material that at least partially inhibits adhesion of organic materials following implantation.

In these aspects, the coating can be continuous over at least said portion of the device. In one example, a polyethylene glycol (PEG) may be deposited on the surface.

In a third aspect, the invention is an implantable apparatus for delivering electrical stimulation to an implantee, the apparatus comprising:

a stimulator device that generates stimulation signals; and
an elongate member having at least one electrode supported thereon that receives the stimulation signals and delivers electrical stimulation in response to said signals;

wherein the stimulation at least partially inhibits adhesion of organic molecules to said at least one electrode.

In one embodiment, stimulation is optimised to at least partially inhibit the adhesion of organic molecules to the at least one electrode. The apparatus can be adapted to deliver electrical stimulation to the neural network of the implantee. As used herein, the term "neural network" is to be understood as including the entire nervous system of the implantee, including the peripheral and central nervous systems. The apparatus can, however, also be adapted to deliver electrical stimulation to the tissue surrounding the location of the neurones and around the implantable location of the elongate member.

BRIEF DESCRIPTION OF THE DRAWINGS

By way of example only, the invention is now described with reference to the accompanying drawings:

FIG. 3 depicts an electric current waveform for inhibiting molecular deposition on an electrode array.

DETAILED DESCRIPTION

The power consumption and efficiency of a tissue-stimulating device, such as a Cochlear™ implant, depends on the impedance of the electrodes positioned on the intracochlear electrode array. Factors that are thought to increase the impedance of the electrodes include adsorption of organic molecules onto and around the electrodes and subsequent growth of fibrous tissue on and around the electrodes or on the surrounding elongate member supporting them.

Figure 1:
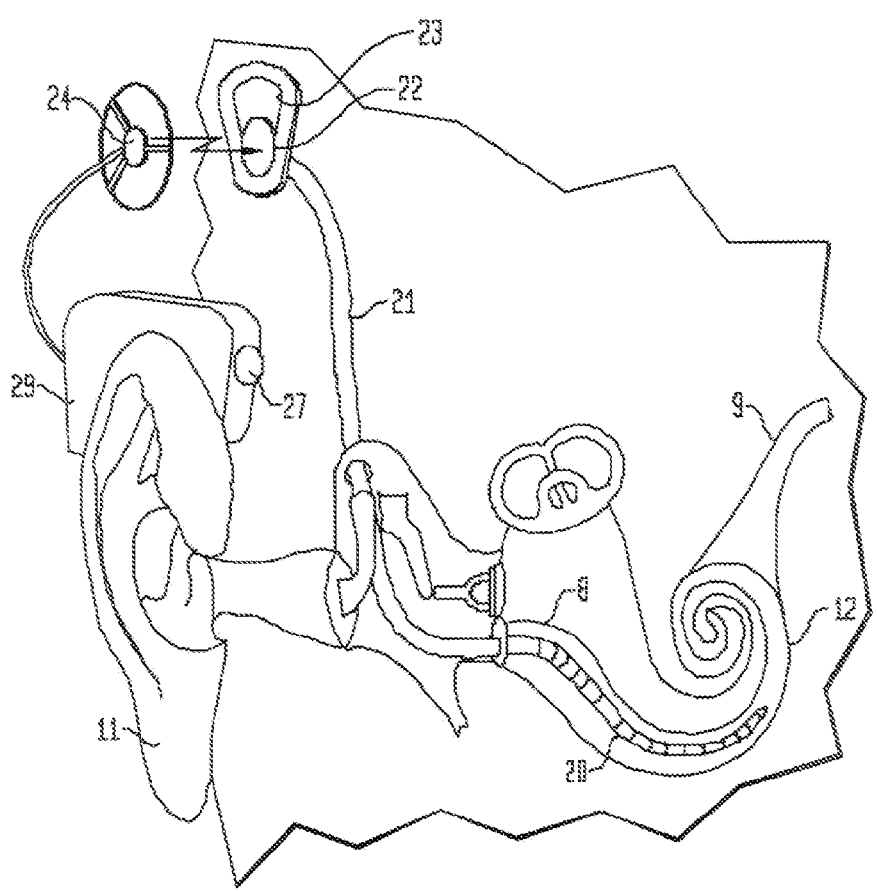
FIG. 1 is a pictorial representation of a hearing implant.
Figure 2:
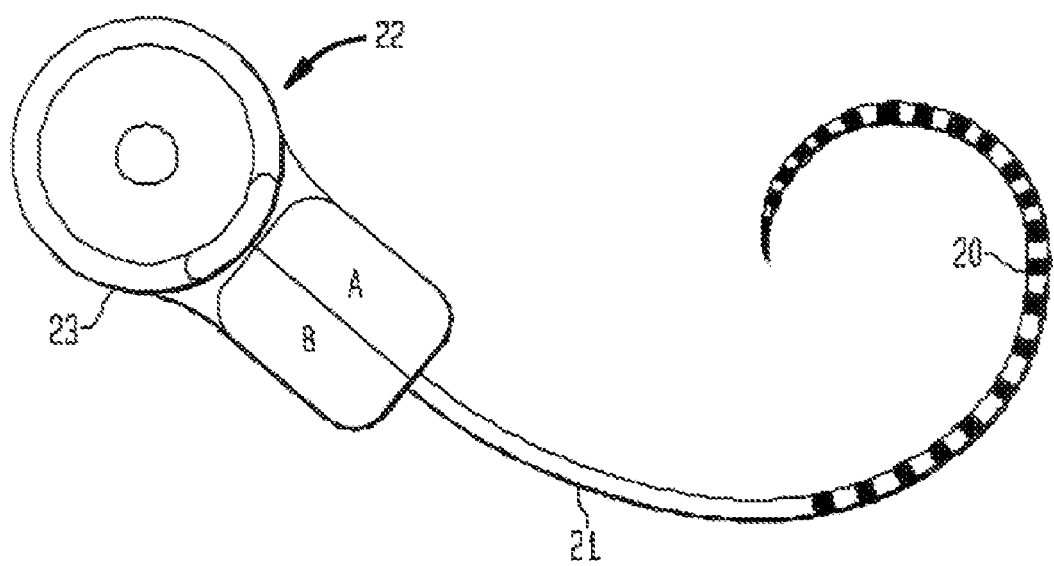
FIG. 2 is a depiction of an implantable component.

One embodiment of a hearing implant is depicted in FIGS. 1 and 2. While for the purposes of this description, a Cochlear™ implant is depicted it will be appreciated that other devices for stimulating other locations of an implantee can be envisaged and are encompassed within the present application.

The hearing implant of FIG. 1 comprises two main components, namely an external component including an external housing containing a speech processor 29, and an internal component including an implanted receiver and stimulator unit 22. The external component includes a microphone 27. The speech processor 29 is, in this illustration, constructed and arranged so that it can be mounted on and fit behind the outer ear 11. It will be understood that in an alternative version, the housing for the speech processor 29 and/or the microphone 27 may be worn on the body. Attached to the speech processor 29 is an external antenna coil 24 which transmits electrical signals to the implanted unit 22 via a frequency modulated (FM) radio frequency (RF) link.

The implanted component includes a receiver antenna coil 23 for receiving power and data from the transmitter coil 24. A cable 21 extends from the implanted receiver and stimulator unit 22 to the cochlea 12 and terminates in an electrode array 20. The data signals thus received are decoded and applied as current pulses by the array 20 thereby stimulating the auditory nerve 9.

It will be appreciated that whilst FIG. 1 depicts a system having internal and external components, the present invention is equally applicable to a fully implantable system whereby the components are contained in one or more housings implanted within the recipient.

In addition to the array 20 being capable of delivering auditory stimuli to the modiolus 8, the hearing implant is adapted to deliver stimulation that at least partially inhibits organic molecule adhesion to the electrodes of the array. As depicted in FIG. 2, the housing of the unit 22 can comprise a portion A that contains what would be regarded as the traditional circuitry of the implant so that the implant can function as a traditional hearing implant. It also comprises a portion B that houses appropriate circuitry to allow the electrode array 20 to deliver the stimulation that inhibits organic molecular adhesion as defined herein.

The inhibitory stimulation may have a magnitude less than the auditory perception threshold of the implantee and as such may not cause the implantee to perceive a sound which is in contrast to the case when the implant delivers an auditory stimuli.

The inhibitory stimulation can be delivered after surgical implantation of the implant and prior to activation of the implant to deliver auditory informative stimuli to the implantee. Once auditory informative stimuli is delivered, the implant can operate so as to never again deliver inhibitory stimulation, with the auditory stimuli themselves acting to inhibit tissue growth. The apparatus could though be operable so as to deliver such inhibitory stimulation at times when the implant is not delivering auditory informative stimuli. For example, the implant might deliver inhibitory stimulation to the cochlea overnight when the implantee does not wish to receive auditory informative stimuli or when the apparatus is inactive for other reasons.

It is anticipated that it would be desirable to deliver the inhibitory stimulation as soon as possible after implantation of the array 20. It is even envisaged that the array 20 could be operable so as to be delivering inhibitory stimulation during implantation of the array 20. The length of time that the implantee receives the inhibitory stimulation will be dependent on factors such as how quickly it is decided to activate the implant for delivery of auditory informative stimuli. It is currently envisaged that the inhibitory stimulation may be delivered for up to 12 weeks following implantation of the array 20 at which point the implant is typically activated or "switched on". This is due to the fact that the immune responses that cause fibrous tissue growth are triggered by any damage to the cochlea structures which may be caused during insertion of the array 20. These immune responses are typically complete after 12 weeks and as such fibrous tissue growth after this time will be minimal.

In a further embodiment, for instances where individuals have not received inhibitory stimulation immediately following implantation, an inhibitory stimulation of a different type may be applied. This may be applied in the fonm of a concentrated stimulation for a specific period of time at an intensity and rate to partially or wholly remove fibrous tissue from the electrodes. Following this concentrated stimulation, normal inhibitory stimulation may be employed to prevent any further growth.

As depicted by FIG. 3, the inhibitory stimulation can comprise an anodic pulse. The anodic pulse may be in the form of a large positive potential excursion such that it desorbs organic molecules from the one or more electrodes. This would also result in oxidisation of the electrode. The anodic pulse can be followed by a cathodic pulse. Again, the cathodic pulse can be in the form of a large negative potential such that it dissolves the oxide back to its metal state. The stimulation thus can have an oscillating waveform. It will be appreciated that the waveform can be more complex and/or asymmetric.

For example, the waveform can be square, as depicted in FIG. 3, or may be sinusoidal where the anodic and cathodic pulse may be symmetrical or asymmetrical but in any case charge balanced. The waveform may also have phases of much wider duration than that shown (with less current to maintain the sub-threshold level) and may even be superimposed with a normal auditory stimulus waveform for delivering sound signals.

It will also be appreciated that the rate of application of inhibitory stimulus pulses may be very low (e.g. one per minute) in order to conserve the power efficiency of the device. In this regard, the specific rate of application will be optimised to be as low as possible in order to retain the electrodes clear of fibrous tissue.

The implantable unit 22 of the implant could be modified so as to house a power source, such as one or more rechargeable batteries. This power source can have sufficient power to allow the implant to deliver inhibitory stimulation even when the external component is not being used and the implantee is unable to receive auditory informative stimuli. This is advantageous as it allows the system to deliver said stimulation such as when the implantee is asleep.

In this regard, the electronics housed in the implantable unit can be provided with a clock, controlling the overall operation of the implant. This clock can control the timing as to when the inhibitory stimulation is delivered. This clock can be programmable to operate in "real time" such that the recipient can receive the inhibitory stimulation at times when the recipient is asleep or not receiving auditory informative stimuli. Such a clock would ideally take into consideration time changes and personal settings, such as shift work etc, and would therefore be controllable through an external device, such as the conventional external speech processor 29. Further, the electronics may also be programmed to initiate the inhibitory stimulus whenever auditory stimulus ceases.

The electrodes and/or the elongate member of the array 20 can be coated with a coating that at least partially inhibits adhesion of organic molecules to said device following implantation. Such a coating can be present on an array 20 of a device that can deliver inhibitory stimulation. The coating could, however, be used on a hearing implant array or the array of other tissue-stimulating devices that are not adapted to deliver inhibitory stimulation.

An inhibiting coating can be a hydrophilic polymer or a derivative thereof. Examples of suitable polymers include water-soluble linear or branched polymers including but not limited to polyethylene glycol (PEG) and polypropylene oxide (PPO) and similar linear and branched polymers and derivatives thereof.

In these embodiments, the elongate member can be covered with a continuous coating. In another embodiment, some or all of the elongate member can be covered by a coating that has a surface pattern. The surface pattern can influence the tissue growth, by inhibiting such growth, encouraging such growth and/or influencing the direction of any growth.

Figure 4A:
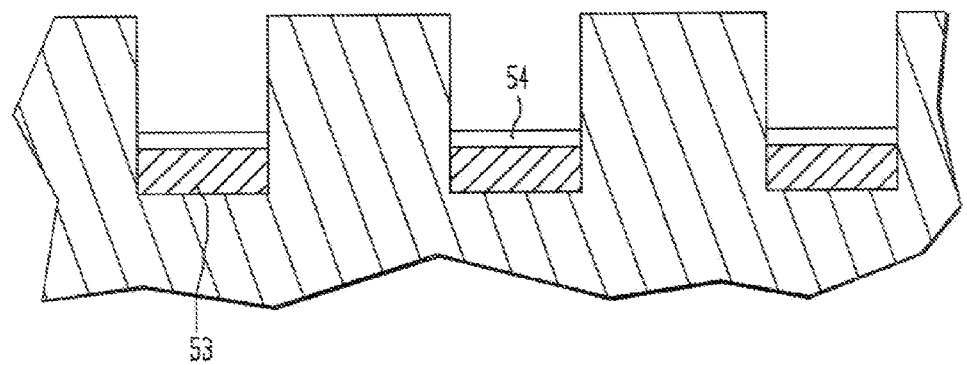
FIGS. 4a and 4b depict electrodes of an array having a coating that inhibits molecular deposition.
Figure 4B:
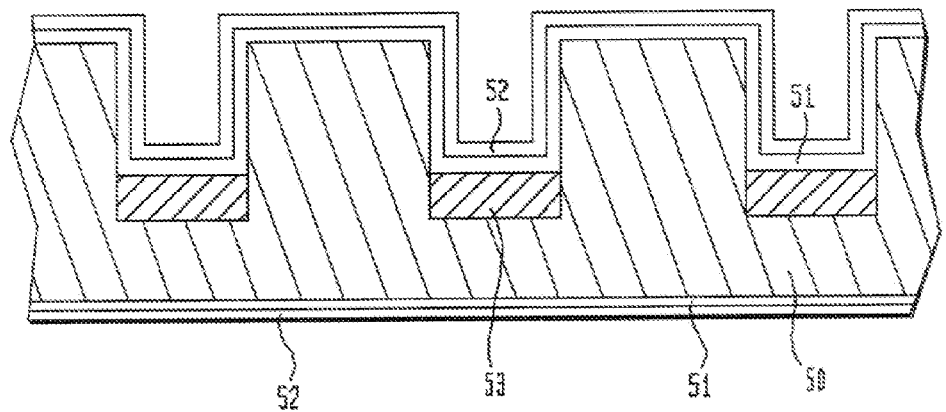

As depicted in FIG. 4a and 4b, the electrodes 41 can each have a layer of biocompatible and water soluble polyethylene glycol (PEG) 42, or a PEG derivative, deposited thereon. PEG has the following structure

Derivatives of the hydrophilic polymer may be formed by chemical modification and/or conjugation reactions. For example, derivatives of PEG and PPO include but are not limited to thiols, silanes, ethers, esters, amides, amines, acids and aldehydes. The PEG can include functional groups that enable functional bonding between the coating and the material of the electrodes 41. Where the electrode is formed from gold or platinum or has a surface formed from such a material, the PEG structure can include, for example, thiol or silane functional groups.

In the depicted embodiment, the PEG coating has a melting point greater than room temperature and indeed has a melting point higher than 50° C. As the electrode array 20 is kept at room temperature, a drop of melted PEG can be deposited on the electrodes 41 that are each positioned in a respective recess 43. Once deposited, the PEG will cool and solidify promptly leaving a temporary coating on the electrodes 41.

As depicted by FIG. 4b, the quantity of coating applied in each electrode recess can be such that the outer surface of the solidified coating 42 is below the top of the recess, at or about the top of the recess or can be proud of the top of the recess 43.

As the depicted coating 42 is soluble, the coating is expected to have a limited lifespan following implantation. In this regard, the lifespan can be less than 3 months, more preferably less than 2 months. It could also be arranged that .the coating is designed to last until about the expected date when the implant is to be activated. In this regard, the implant is typically activated within 12 weeks following implantation.

The coating 42 can also be removable by an electrochemical cleaning process, such as the pulsing sequence depicted in FIG. 3. As described, this can comprise increasing the potential of the electrodes 41 to a level where oxidation of the electrode material occurs and reducing the potential to a level where the oxide is reduced back to a metallic state. During the oxidation step, any remnants of the coating are stripped off the electrode surface leaving it in an oxidised state that is subsequently reduced back to the metal. It is to be appreciated that a cleaning action may be achieved without fully oxidising and reducing the surface of the electrodes.

The coating can also be in the form of a gel or gel-like mass. To form this, the coating material prior to deposition can be dissolved in a suitable solvent, such as water, at, for example, an elevated temperature and then caused to solidify by allowing the material to reduce in temperature to a temperature below the melting point of the material. The solvent can contain a solute, such as a salt, for example, sodium chloride. This results in the coating having at least a degree of electrical conductivity.

Figure 5A:
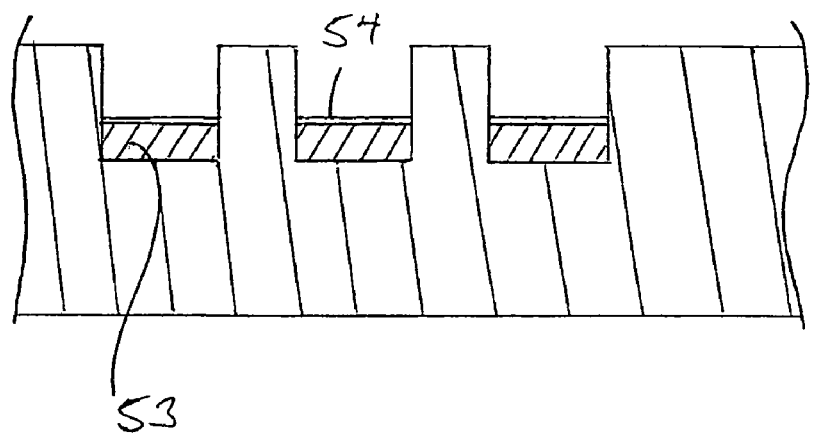
FIGS. 5a and 5b depict electrodes and an array, respectively, having a monolayer coating.
Figure 5B:
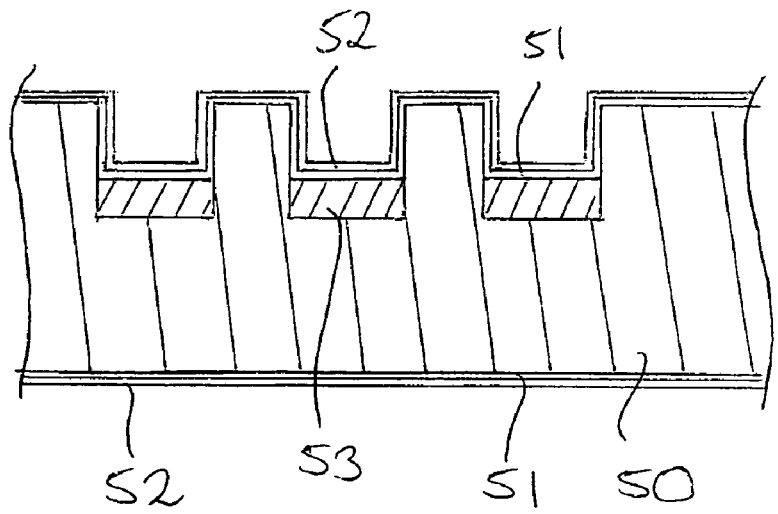

Each of the electrodes and/or the elongate member of the array can have a coating that is semi-permanent or permanent. Such coatings can have a property of at least allowing partial access, more preferably unimpaired access, of ions to the electrode surface, while minimising protein adsorption at the same surface. Such a coating can comprise a self-assembled monolayer. Such a monolayer 54 can be coated only on the electrodes 53 (as depicted in FIG. 5a) or can be coated over all of the array 20 (as depicted in FIG. 5b). Where the elongate member of the array is formed of a silicone 50, a layer of a suitable metal can be firstly applied to the elongate member. In one example, this layer can be gold 51 and have a thickness of less than 10 nanometers. Such a layer 51 may be coated using a sputtering or evaporation technique. Due to its thinness, it is anticipated that the layer 51 would overall be electrically conductive and as such would not affect the electrical functionality of the device. A monolayer coating 52 would then be deposited on the layer 51 of suitable metal.

The elongate member of the array 20 can be formed from a suitable biocompatible material. As already described, that material can be a silicone, such as Silastic MDX 4-4210. In another embodiment, the elongate member can be formed from a polyurethane.

Each electrode is also preferably formed from a biocompatible material, such as platinum. In one embodiment, the electrode array 20 can comprise 22 platinum electrodes spaced along the elongate member.

The implant system can also include one or more capacitively coupled extracochlea electrodes to support monopolar stimulation as is known in the art.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. An implantable tissue-stimulating device for an implantee comprising:
   an elongate member; and
   at least one electrode disposed on said elongate member,
   wherein at least a portion of the device is coated, prior to implantation in the implantee, with a hydrophilic polymer configured to at least partially inhibit adhesion of body tissue to said device following implantation, and wherein the coating is removable, after implantation, by an electrochemical cleaning process during which potential of one or more of said at least one electrode is increased and then decreased.

2. The device of claim 1, wherein the coating is polyethylene glycol (PEG).

3. The device of claim 1, wherein the coating has functional groups that enable functional bonding between the coating and said portion of the device.

4. The device of claim 3, wherein the functional groups enable functional bonding between the coating and an electrically active electrode surface.

5. The device of claim 4, wherein the electrically active electrode surface is gold or platinum.

6. The device of claim 1, wherein said one or more of said at least one electrode is coated with said coating.

7. The device of claim 1, wherein a portion of the elongate member is coated with the coating.

8. The device of claim 1, wherein each of said one or more electrodes is positioned in a recess formed in the elongate body.

9. The device of claim 8, wherein the coating is applied to each of said one or more electrodes in a liquid form which is configured to become a solid subsequent to application.

10. The device of claim 1, wherein the coating is bioresorbable following implantation.

11. The device of claim 1, wherein said coating comprises at least one solute.

12. The device of claim 1, wherein the coating is configured to be a self-assembled monolayer.

13. The device of claim 12, wherein where the elongate member is formed of a silicone, and a layer of a suitable metal is applied to the elongate member prior to coating with the monolayer.

14. The device of claim 1, wherein the tissue-stimulating device is a cochlear implant.

15. A method of modifying the surface of at least a portion of an implantable tissue stimulating device, the method comprising:
   providing the tissue stimulating device having at least one electrode;
   coating said portion with hydrophilic polymer configured to at least partially inhibit adhesion of body tissue to said surface following implantation;

following implantation, causing an increase in potential of said at least one electrode followed by a decrease in potential of said electrode, so as to remove the hydrophilic polymer.

16. An implantable apparatus for delivering electrical stimulation to an implantee, the apparatus comprising:
an elongate member, having at least one electrode supported thereon configured to receive an inhibitory stimulation signal and to deliver said inhibitory stimulation signal to the implantee, wherein said inhibitory stimulation signal is configured to inhibit adherence of body tissue on said implantable device; and
a stimulator device configured to generate said inhibitory stimulation signal, wherein said inhibitory stimulation signal is configured to have a magnitude below the auditory perception threshold of the implantee, wherein said inhibitory signal comprises at least one pair of anodic and cathodic phases and is configured to at least partially inhibit adhesion of body tissue to said elongate member in a region proximal the at least one electrode, and further wherein said stimulator device is configured to generate said inhibitory stimulation signal after implantation of said apparatus.

17. The apparatus of claim 16, wherein the apparatus is configured to deliver stimulation to tissue surrounding the elongate member.

18. The apparatus of claim 16, wherein the elongate member is positioned and arranged to directly deliver stimulation to the auditory system of the implantee via one or more of the at least one electrode.

19. The apparatus of claim 18, wherein the elongate member is configured to be implanted in the cochlea of the implantee.

20. The apparatus of claim 19, wherein said apparatus is configured to deliver said stimulation prior to activation of said apparatus for delivery of said auditory informative stimuli to the implantee by said activated apparatus.

21. The apparatus of claim 20, wherein following said activation of said apparatus, said apparatus ceases further delivery of said stimulation configured to inhibit body tissue adhesion.

22. The apparatus of claim 21, wherein said apparatus is further configured to deliver said stimulation during periods when said apparatus is not delivering auditory informative stimuli.

23. The apparatus of claim 18, further comprising:
a sensor operatively coupled to said stimulator device configured to automatically activate and deactivate generation of said inhibitory stimulation signal by said stimulator device based on detection of said auditory informative stimuli on said elongate member.

24. The apparatus of claim 16, wherein said anodic phase is configured to oxidize one or more of said at least one electrodes thereby desorbing body tissue from said one or more electrodes, and said cathodic phase is configured to dissolve the oxide back to its metal state.

25. The apparatus of claim 16, further comprising:
an implanted power source configured to power said stimulator device independent from an external power source.

26. The apparatus of claim 16, further comprising:
a clock circuit operatively coupled to said stimulator device configured to automatically activate and deactivate said stimulator device according to a pre-programmed set of instructions.

27. A method for inhibiting adherence of body tissue on an implantable medical device having a stimulator device and at least one electrode comprising:
implanting the implantable medical device in an implantee; and
delivering a stimulation signal, configured to have a magnitude below the auditory perception threshold of the implantee, to the implantee via the at least one electrode, the inhibitory stimulation signal comprising at least one pair of anodic and cathodic phases and being configured to at least partially inhibit adhesion of body tissue to the implanted medical device.

28. The method of 27, wherein delivering said signal is concurrent with said implanting the medical device.

29. A method for at least partially removing adhered body tissue on an implantable medical device having a stimulator device and at least one electrode comprising:
providing the implanted medical device in an implantee; and
delivering to the implantee via the electrode a concentrated stimulation signal comprising a plurality of anodic and cathodic phases and being configured to at least partially remove adhered body tissue from said implanted device, and further configured to comprise only non-auditory-informative stimuli.

30. An implantable apparatus for delivering electrical stimulation to an implantee, the apparatus comprising:
an elongate member having at least one electrode supported thereon configured to deliver electrical stimulation to the implantee; and
a stimulator device configured to generate an inhibitory stimulation signal having a magnitude below the auditory perception threshold of the implantee wherein said stimulation signal is configured to inhibit growth of body tissue on said at least one of said elongate member and said at least one electrode.

31. An implantable apparatus for delivering electrical stimulation to an implantee, the apparatus comprising:
an elongate member having at least one electrode supported thereon configured to receive a stimulation signal and to deliver electrical stimulation in response to said received signal;
a stimulator device configured to generate said stimulation signal wherein the stimulation signal comprises at least one pair of anodic and cathodic phases and is configured to at least partially inhibit adhesion of body tissue to said elongate member in a region proximal the at least one electrode; and
a coating disposed on at least a portion of said elongate member prior to implantation, wherein said coating is configured to at least partially to inhibit adhesion of body tissue to said device following implantation and wherein the coating is removable, after implantation, by an electrochemical cleaning process during which potential of one or more of said at least one electrode is increased and then decreased.

32. The apparatus of claim 31, wherein said coating comprises a hydrophilic polymer.

* * * * *